United States Patent
Wei et al.

(10) Patent No.: US 8,178,157 B2
(45) Date of Patent: May 15, 2012

(54) GAS SENSOR AND MANUFACTURING METHOD THEREOF

(75) Inventors: Bee-Yu Wei, Hsinchu (TW); Hong-Jen Lai, Hsinchu (TW); Pi-Guey Su, Hsinchu (TW); Ren-Jang Wu, Hsinchu (TW); Hong-Ming Lin, Hsinchu (TW); Yi-Lu Sun, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/846,562

(22) Filed: Jul. 29, 2010

(65) Prior Publication Data

US 2010/0310792 A1    Dec. 9, 2010

Related U.S. Application Data

(60) Division of application No. 10/889,271, filed on Jul. 12, 2004, now abandoned, and a continuation of application No. 12/844,300, filed on Jul. 27, 2010.

(30) Foreign Application Priority Data

Aug. 27, 2003 (TW) ............................... 92123548 A

(51) Int. Cl.
     *B05D 5/12*      (2006.01)
(52) U.S. Cl. ............... 427/115; 427/126.3; 427/240; 427/383.1; 427/421.1; 427/430.1

(58) Field of Classification Search .................. 427/115, 427/126.3, 240, 383.1, 421.1, 430.1
See application file for complete search history.

(56) References Cited

U.S. PATENT DOCUMENTS

| | | | |
|---|---|---|---|
| 4,535,315 A | 8/1985 | Sakai | |
| 2002/0127406 A1* | 9/2002 | Sachdev et al. | 428/413 |
| 2003/0099575 A1* | 5/2003 | Sung et al. | 422/88 |
| 2004/0167009 A1 | 8/2004 | Kuntz et al. | |
| 2008/0105544 A1 | 5/2008 | Shigematsu et al. | |

OTHER PUBLICATIONS

Hsu et al., "Gas Sensing Behavior at Room Temperature of Nanostructured CNT/SNO2 Hybrid Sensors", Master Thesis Department of Materials Engineering Tatung University—Jun. 2003.*

Wei, et al.; "A Novel SnO2 Gas Sensor Doped with Carbon Nanotubes Operating at Room Temperature;" Sensors and Actuators B 101; 2004; pp. 81-89.

Han, et al.; "Coating Single-Walled Carbon Nanotubes with Tin Oxide;" NANO Letters, vol. 3, No. 5; Apr. 2, 2003; pp. 681-683.

* cited by examiner

*Primary Examiner* — Brian K Talbot
(74) *Attorney, Agent, or Firm* — Thomas|Kayden

(57) ABSTRACT

A gas sensor and manufacturing method thereof. The gas sensor includes a substrate, a pair of electrodes disposed on the substrate, and a gas sensing thin film covering the electrodes, the gas sensing thin film is made up of carbon nanotubes and tin oxide.

13 Claims, 4 Drawing Sheets

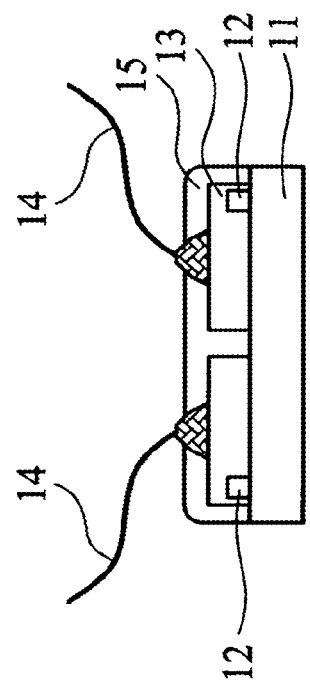
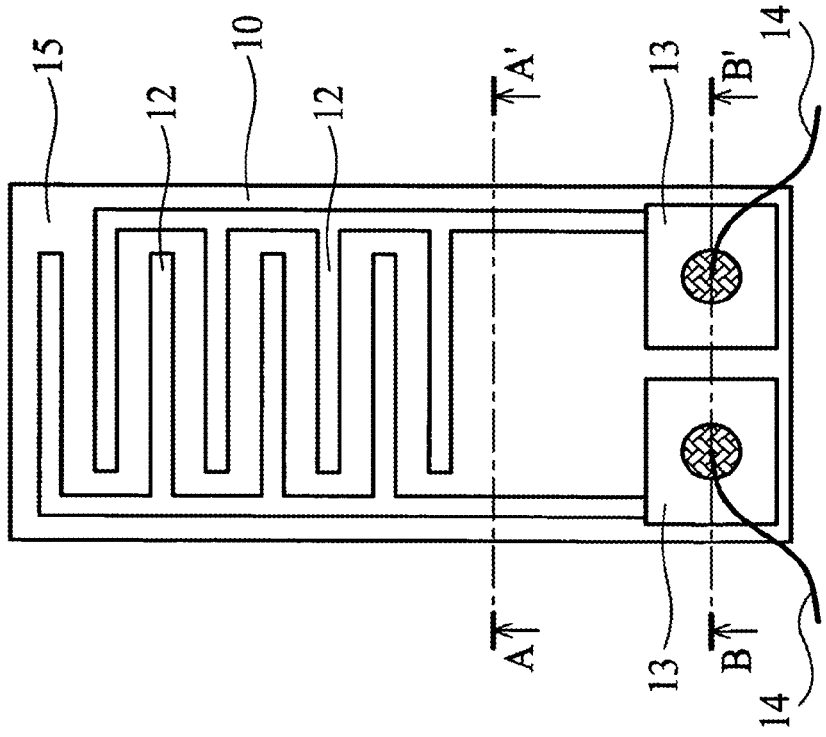
FIG. 1B
FIG. 1C
FIG. 1A

US 8,178,157 B2

GAS SENSOR AND MANUFACTURING METHOD THEREOF

CROSS REFERENCE TO RELATED APPLICATIONS

This application is a Division of pending U.S. patent application Ser. No. 10/889,271, filed Jul. 12, 2004, and entitled "gas sensor and manufacturing method thereof," which claims priority of Taiwan Patent Application No. 92123548, filed Aug. 27, 2003. This application is also a continuation of U.S. patent application Ser. No. 12/844,300, filed Jul. 27, 2010. The entirety of each of the foregoing applications are incorporated by reference herein.

BACKGROUND OF THE INVENTION

1. Field of the Invention

The present invention relates to a gas sensor and manufacturing method thereof. More particularly, the present invention relates to a gas sensor using carbon nanotubes and metal oxide as a sensing film.

2. Description of the Related Arts

Naturally occurring gases such as carbon monoxide (CO), nitrogen oxides ($NO_x$), hydrogen sulfide ($H_2S$), or methane ($CH_4$) can be hazardous to humans. These toxic gases are colorless and tasteless and cannot be easily detected by human senses. When the concentration of toxic gases in an environment exceeds an allowable range, symptoms of headache, dizziness, sickness, or even shock or death can result. Gas analyzers provide real-time monitoring of gas content in airtight or unventilated environments, providing timely notification when the concentration of toxic gases exceeds a threshold.

Atomic/molecular absorption spectrometry, atomic/molecular fluorescence spectrometry, and gas chromatography are commonly used in chemical laboratory and quality control for gas analysis. These gas analysis instruments have the advantages of high accuracy, high sensitivity, and low detection limit; however, their application is limited due to a large profile with low portability, high power consumption, structural complexity, and high cost. It is, therefore, important to provide a simply equipped gas sensor.

Gas sensors detect gas concentration and convert the concentration into an electric signal. Traditional gas sensors include, for example, electrochemical gas sensors and metal oxide semiconductor gas sensors.

Electrochemical gas sensors detect gases by measuring an electric current or pressure produced by an oxidation reduction reaction resulting from the dissolution of the target gas in a liquid electrolyte between two electrodes of an electrochemical tank. These gas sensors are applicable at room temperature; however, they have a short lifetime due to the corrosive property of the liquid electrolyte. In addition, calibration of the sensor baseline is required since chemical buildup at the reference electrode may cause baseline drift. Moreover, electrochemical gas sensors are usually costly.

Metal oxide semiconductor (MOS) gas sensors utilize resistance changes depending on gas contents absorbed by metal oxide to detect gas concentration changes. They can be simply prepared or combined with microelectromechanical systems (MEMS) to be portable. With these properties, MOS gas sensors are highly useful. A MOS gas sensor can include a ceramic substrate, a pair of measuring electrodes, a sensing layer, and a heater. The sensing layer is usually a polycrystal and porous layer of metal oxides such as $SnO_2$, ZnO, $Fe_2O_3$, $In_2O_3$, $WO_3$ and the like. Examples of $SnO_2$ base MOS gas sensor includes U.S. Pat. Nos. 4,535,315, 5,185,130, 5,273,779, 5,427,740, 5,624,640.

U.S. Pat. No. 4,535,315 discloses a process for the manufacture of a sensor including preparing a fine tin oxide powder using stannic chloride, preparing a paste by dissolving the tine oxide powder into ethylene glycol, applying the paste on a ceramic substrate, and baking the substrate to form a $SnO_2$ sensing layer. The $SnO_2$ gas sensor selectively detects alkane gases such as methane gas, propane gas and butane gas. The detection of alkane gas is based on that the absorbed alkane gas decreases the electrical resistance of the sensor. However, heat desorption of the absorbed gases at 200 to 500° C. is required, and the sensitivity of the sensor is not satisfactory.

In order to enhance the sensitivity of $SnO_2$ gas sensor, addition of other elements to the $SnO_2$ layer was proposed by U.S. Pat. No. 5,185,130. The proposed sensor selectively detects nitrogen oxide and hydrogen gas in an atmosphere containing carbon monoxide, methane, nitrogen oxide, and hydrogen gas. The preparation of the sensor includes depositing a thin film of tin and bismuth on a ceramic substrate by vacuum evaporation followed by thermally treating the film deposited on the substrate. The thermal treatment includes the following cycle: increasing the temperature from ambient to 300-350° C. over 5-35 minutes and maintaining the temperature for 1-3 hours; increasing the temperature to 400-450° C. over 2.5-3.5 hours and maintaining the temperature for 2.5-3.5 hours; increasing the temperature to 470-500° C. over 4-6 hours and maintaining the temperature over 3-4 hours. The prepared sensor contains $Bi_2O_3$ of 5-7% by atomic weight. High throughput production cannot be easily achieved due to the requirement of vacuum equipment; the thermal treatment also increases the cost; in addition, the working temperature of the sensor is 200-500° C.

Another example of the enhancement of sensitivity was proposed by U.S. Pat. No. 5,273,779. The addition of noble metals to the $SnO_2$ substrate enhances the sensitivity of the sensor via the catalyst effect. The disclosed $SnO_2$ gas sensor for the detection of alcohol and $H_2$ is prepared by immersing an $Al_2O_3$ substrate into an organic tin solution, forming a buffer layer on the substrate by spin coating, sintering the buffer layer at 800° C. over 5 hours, immersing the substrate into an organo-metallic solution of Au and Sn, forming a $SnO_2$ gas sensing layer by spin-coating and heat-treating at 800° C. over 5 hours, screen-printing electrodes with heat treatment at 600° C., immersing the substrate into a organo-metallic solution of Au and Pd, forming a catalyst layer on the $SnO_2$ layer with heat treatment at 600° C., and coating a second gas sensing layer (with a organo-metallic solution of La and Sn) on the catalyst layer with heat treatment at 600° C. over for 5 hours. The process is complicated and costly due to noble metals and multiple heat treatments. In addition, the gas sensor cannot be used at room temperature.

U.S. Pat. No. 5,427,740 discloses a $SnO_2$ gas sensor for the detection of $H_2$, CO, and $CH_4$. The preparation of this gas sensor is similar to U.S. Pat. No. 4,535,315, except for that the slurry including Sb is heat treated at 1100-1600° C. prior to coating on the substrate. A tin oxide gas sensing layer containing $Sb_2O_3$ is formed after 800-1000° C. heat treatment. This preparation is costly due to the heat treatment, and the gas sensor also needs to be used at 280-400° C.

U.S. Pat. No. 5,624,640 discloses a sensitivity-enhanced gas sensor for the detection of NO, $NO_2$, and $N_2O_4$ with a $SnO_2$ gas sensing layer containing Ta, Nb, Sb, or W. The $SnO_2$ layer is covered by a gas convert layer composed of $TiO_2$, $ZrO_2$, $SiO_2$, or $Al_2O_3$ and a catalyst such as Pt. Nitrogen oxide is detected by the gas convert layer and oxidized to $NO_2$ or $N_2O_4$, and $NO_2$ or $N_2O_4$ is then detected by the $SnO_2$ layer. This gas sensor is costly and has to be used at 180-400° C.

The drawbacks of these gas sensors include low sensitivity, selectivity, and stability with gas. To accelerate desorption of gas absorbed on the sensing layer of metal oxide, MOS gas sensors are usually applied at higher temperatures such as 300 to 450° C. to enhance recovery time. Longtime operation at high temperatures may, however, causes irreversible changes in the electrical properties of metal oxides, leading to signal drift. The heating requirement of these gas sensors also evokes several problems such as increased size of the gas sensor, power consumption, and temperature control. Therefore, the cost of the gas sensor cannot be reduced.

Nano-materials have advantage properties associated with their special surface and volume effects and can be used in porous sintered films to increase reaction surface and sensitivity. U.S. Pat. No. 6,059,937 (2000) discloses a $SnO_2$ gas sensor prepared by depositing a $SnO_2$ nano-level film on a ceramic substrate by ion beam sputtering, and depositing Pt or Pd electrodes on the substrate. The sensor detects $CH_4$ and $C_3H_8$ at a lower temperature, such as 150° C. for $CH_4$ and 190° C. for $C_3H_8$; however, ion beam sputtering and Pt or Pd electrodes are costly, and the working temperature cannot be reduced to room temperature. U.S. Pat. No. 6,134,946 (2000) discloses a $SnO_2$ gas sensor for the detection of carbon monoxide, hydrocarbons, and organic vapors. The preparation comprises depositing tin oxide sol on Pt electrodes of a sensor. The thin film of tin oxide has a nano-crystalline structure with good stability. However, the sensor still cannot be used at room temperature.

The above mentioned sensors have a common problem—unable to be used at room temperature; therefore, researchers are focusing on the study of a sensor with low working temperature. An example is U.S. Pat. No. 5,448,906 which discloses a gas sensor with a working temperature of room temperature. A light source such as UV or LED can be equipped on the gas sensor. When sensing gases, the light induces gas desorption from the sensing film. The disadvantage of the sensor is the difficulty of controlling sensor temperature since the temperature of the sensor is increased by lightening time. In addition, the design for light induction is complicated and the cost cannot be reduced. There is, therefore, still a need for a gas sensor with low cost and workable at room temperature.

SUMMARY OF THE INVENTION

It is therefore a primary object of the present invention to provide a gas sensor with high sensitivity, good repeatability and rapid recovery rate at room temperature. The gas sensor of the present invention solves the problems of conventional semiconductor metal oxide gas sensors that require heat desorption of the gas chemically absorbed on the oxide layer. In addition, the sensor of the present invention is economic in preparation.

Accordingly, the present invention provides a gas sensor comprising a substrate, a pair of electrodes on the substrate, and a gas sensing thin film on the electrodes. The gas sensing thin film comprises carbon nanotubes and tin oxide ($SnO_x$), wherein x=1-2, and the ratio of carbon nanotubes and tin oxide is 0.001-5 wt %, preferably 0.001-0.05 wt %.

The present invention also provides a manufacturing method for a gas sensor. The method comprises providing a substrate with a pair of electrodes thereon, application of a mixture of carbon nanotubes and an organic tin compound or tin oxide to the substrate to cover the pair of electrodes, and heat-treating or drying the substrate to obtain a gas sensing thin film comprising carbon nanotubes and tin oxide.

BRIEF DESCRIPTION OF THE DRAWINGS

The present invention will be more fully understood and further advantages will become apparent when reference is made to the following description of the invention and the accompanying drawings in which:

FIG. 1A~1C illustrates the structure of the gas sensor of the present invention, with FIG. 1A a top view, FIG. 1B a cross-section of A-A' in FIG. 1A, and FIG. 1C a cross-section of B-B' in FIG. 1A.

DETAILED DESCRIPTION OF THE INVENTION

Figure 2:
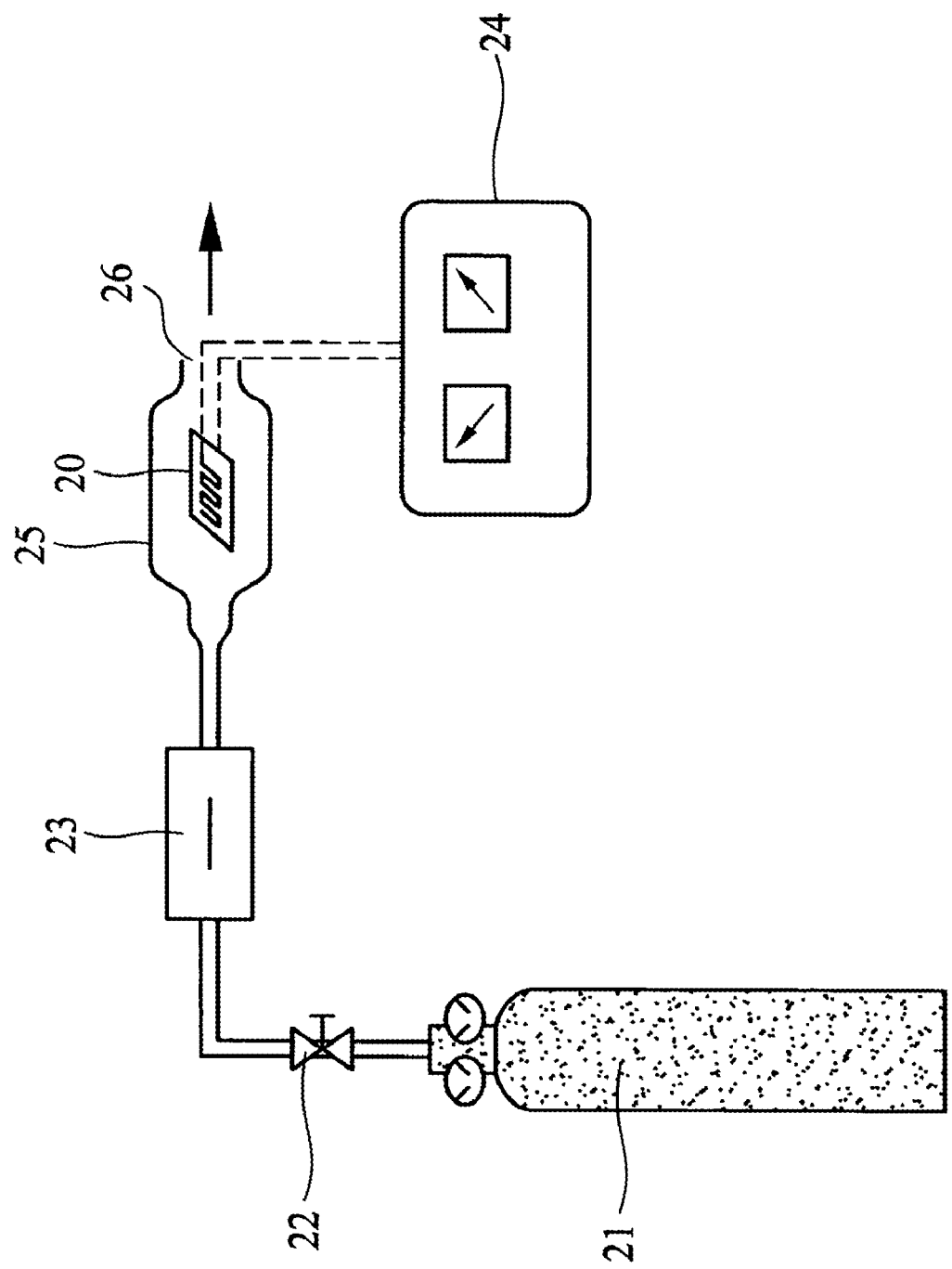
FIG. 2 illustrates disposition of the gas detection apparatus in the example of the invention.

Without intending to limit the invention in any way, the present invention will be further illustrated by the following description.

The present invention provides a gas sensor utilizing a carbon nanotube-containing gas sensing film. Carbon nanotubes have a large surface area for gas adsorption, whereby, when gas molecules are adsorbed, electrical properties of the carbon nanotubes changes. "Nanotube molecular wires as chemical sensors" published on Science (2000) 287, 622 discloses that single-walled carbon nanotubes used as semiconductor field effect transistor are functional at room temperature, however, their preparation is difficult and costly and the detected signal is weak (~$10^{-7}$ A/V).

Manufacture of the gas sensing film of the present invention comprises mixing a small amount of carbon nanotubes into a tin-containing organo-metallic solution to form a suspension, applying the suspension to a substrate with metal electrodes thereon, and heat-treating the substrate to produce a $SnO_2$ sensing film, providing a gas sensor with high sensitivity and rapid recovery at room temperature. Therefore, problems of recovery and sensitivity at room temperature of conventional metal oxide sensing materials are solved.

The gas sensor of the present invention comprises a substrate, a pair of electrodes on the substrate, and a gas sensing thin film on the electrodes. The gas sensing thin film comprises carbon nanotubes and tin oxide ($SnO_x$), wherein x=1-2, and the ratio of carbon nanotubes and tin oxide is 0.001-5 wt %, preferably 0.001-0.05 wt %.

In addition, a manufacturing method of the gas sensor comprises providing a substrate with a pair of electrodes thereon, application of a mixture of carbon nanotubes and an organic tin compound or tin oxide to the substrate to cover the pair of electrodes, and heat-treating or drying the substrate to obtain a gas sensing thin film comprising carbon nanotubes and tin oxide.

In one preferred embodiment of the present invention, the substrate used is non-conducting or insulating material, including, but not limited to, ceramic material such as glass, aluminum oxide, silicon oxide, quartz, or mica, or metal covered with insulating material or semiconductor material. The electrodes in the present invention do not contact each other. Acceptable material of the electrodes includes, but is not limited to, gold, platinum, or silver. In addition, the electrode can be a comb, strip, or helix shape. The more complicated the shape, the more significant the signal will be.

Carbon nanotubes used herein include single-walled carbon nanotubes (SWCNTs) or multi-walled carbon nanotubes (MWCNTs). In a preferred embodiment, the carbon nanotubes are single-walled (SWCNTs).

The organic tin compound in the manufacturing method of the present invention is tin(II)-2-ethylhexanoate, dissolved in an organic solvent, such as 2-ethylhexanoic acid, at 5-20 wt %, preferably 10 wt %. Moreover, the carbon nanotubes of the organo-metallic solution are 0.0001-1 wt %, preferably 0.01 wt %. The carbon nanotubes are dispersed in the organo-metallic solution by ultrasonic or mechanical vibration.

The mixture of the carbon nanotubes and the organic metal oxide is preferably applied to the substrate by spin or dip coating. The oxidation of the mixture on the substrate is performed under an atmosphere containing $O_2$ at 400-700° C. for 20-60 minutes.

The gas sensor of the present invention further comprises an Ag/Pd layer on the end of the electrode as a contact and a pair of signal lines separately connected to the electrodes by the Ag/Pd layer to transport a signal.

Practical examples are described herein.

EXAMPLES

Example 1

Gas Sensor of the Present Invention and Preparation Thereof

As shown in FIG. 1A, the gas sensor 10 of the present invention comprises an aluminum oxide ceramic substrate 11 (10×5 mm), with a pair of comb-shaped, gold electrodes 12 thereon. The electrodes do not contact each other. An Ag/Pd layer 13 is coated at the end of the electrodes 12. The gold electrodes 12 and the Ag/Pd layer 13 are formed by screen printing. A $SnO_2$ gas sensing film 15 covers the gold electrode 12.

First, tin (II) 2-ethylhexanoate was dissolved in 2-ethylhexanoic acid to form an organo-metallic solution at weight percentage 10%. One mg of the single-walled carbon nanotubes (Carbon Nanotechnology Inc., prepared by HiPco process) and 10 g of the organo-metallic solution were mixed. The mixture was vibrated by ultrasonic oscillator for 2 hours to evenly distribute the carbon nanotubes in the solution and form a suspension containing carbon nanotubes. The suspension was then applied to the gold electrode 12 and Ag/Pd layer 13 as shown in FIG. 1 by spin coating at 1000 rpm/min for 20 minutes. The substrate was dried in an oven at 150° C. for 30 minutes to evaporate the solvent of the suspension. The substrate was finally heated in a furnace for half hour with air circulation to dissolve the organo-metallic solution at 500° C., and a microcrystalline and porous $SnO_2$ gas sensing film 15 was formed at a thickness of about 5-10 μm.

Example 2

Preparation of a Conventional Gas Sensor

The conventional gas sensor does not contain carbon nanotubes. Preparation of the conventional gas sensor follows:

Tin (II) 2-ethylhexazoate was dissolved in 2-ethylhexanoic acid to form an organo-metallic solution at weight percentage 10%. The organo-metallic solution was applied to gold electrodes 12 and Ag/Pd layer 13 as shown in FIG. 1. The substrate covered with the solution was then dried at 150° C. for 30 minutes to evaporate the solvent. After that, the substrate was heated in a furnace for half hour with air circulation to dissolve the organo-metallic solution at 500° C., and a microcrystalline and porous $SnO_2$ gas sensing film was formed at a thickness of 5-10 μm.

Example 3

Comparison of the Gas Sensors of the Present Invention and the Conventional Gas Sensor The schematic diagram of the gas detection apparatus in the experiment is shown in FIG. 2. Before testing, the gas sensing film 15 on the Ag/Pd layer 13 as shown in FIG. 1 was scraped and signal lines 14 were soldered to the Ag/Pd layer 13. The gas sensor 20 of the present invention as shown in FIG. 2 was placed in a glass chamber 25. The input of 1010 ppm $NO_2$ gas 21 was controlled by an intake valve 22 and a mass flow controller 23 100 mL/min. The resistor changes were recorded by LCR meter 24. The outlet of the gas flow is shown as 26 in FIG. 2, with results shown in FIGS. 3 and 4.

Figure 3:
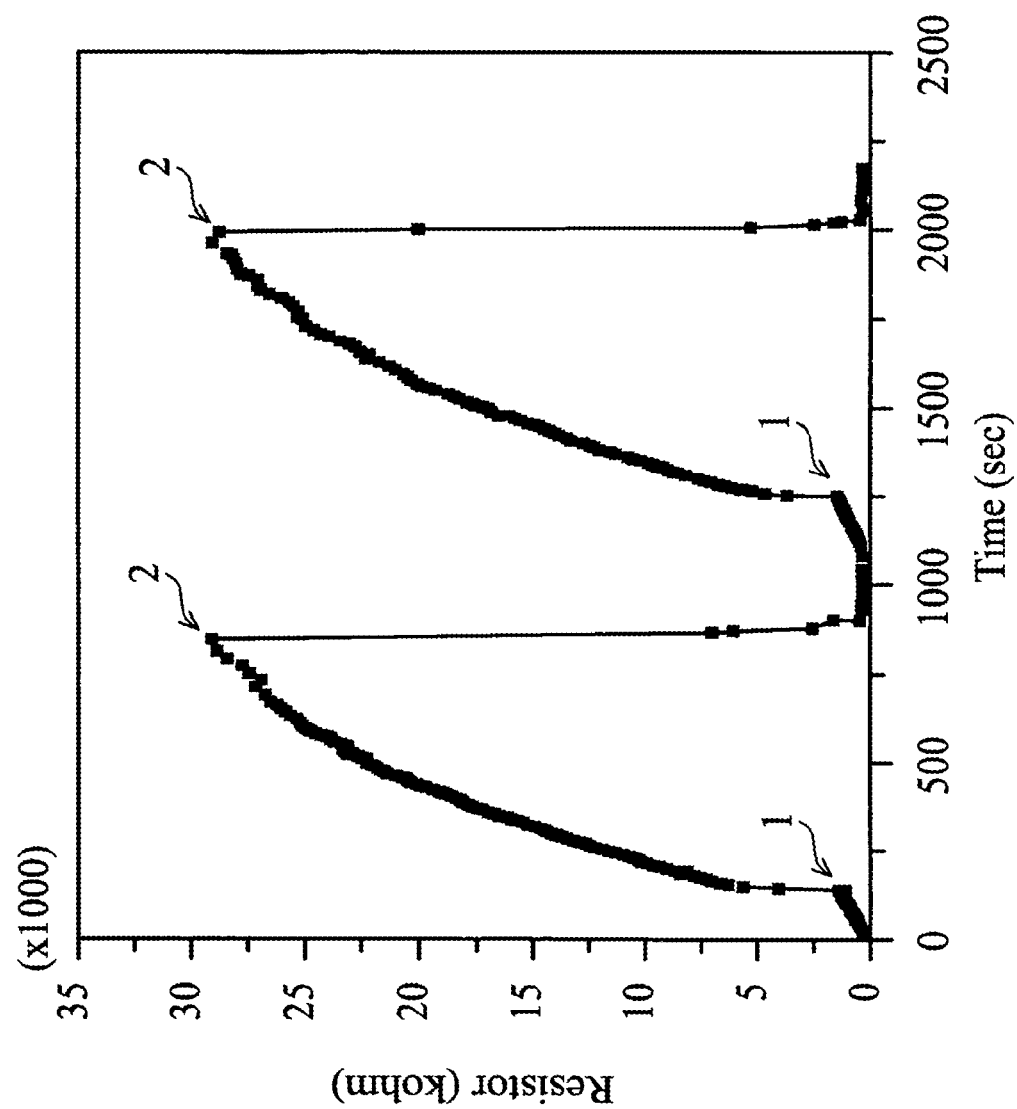
FIG. 3 illustrates the characteristic curve of the gas sensor of the present invention to 1010 ppm $NO_2$ gas.
Figure 4:
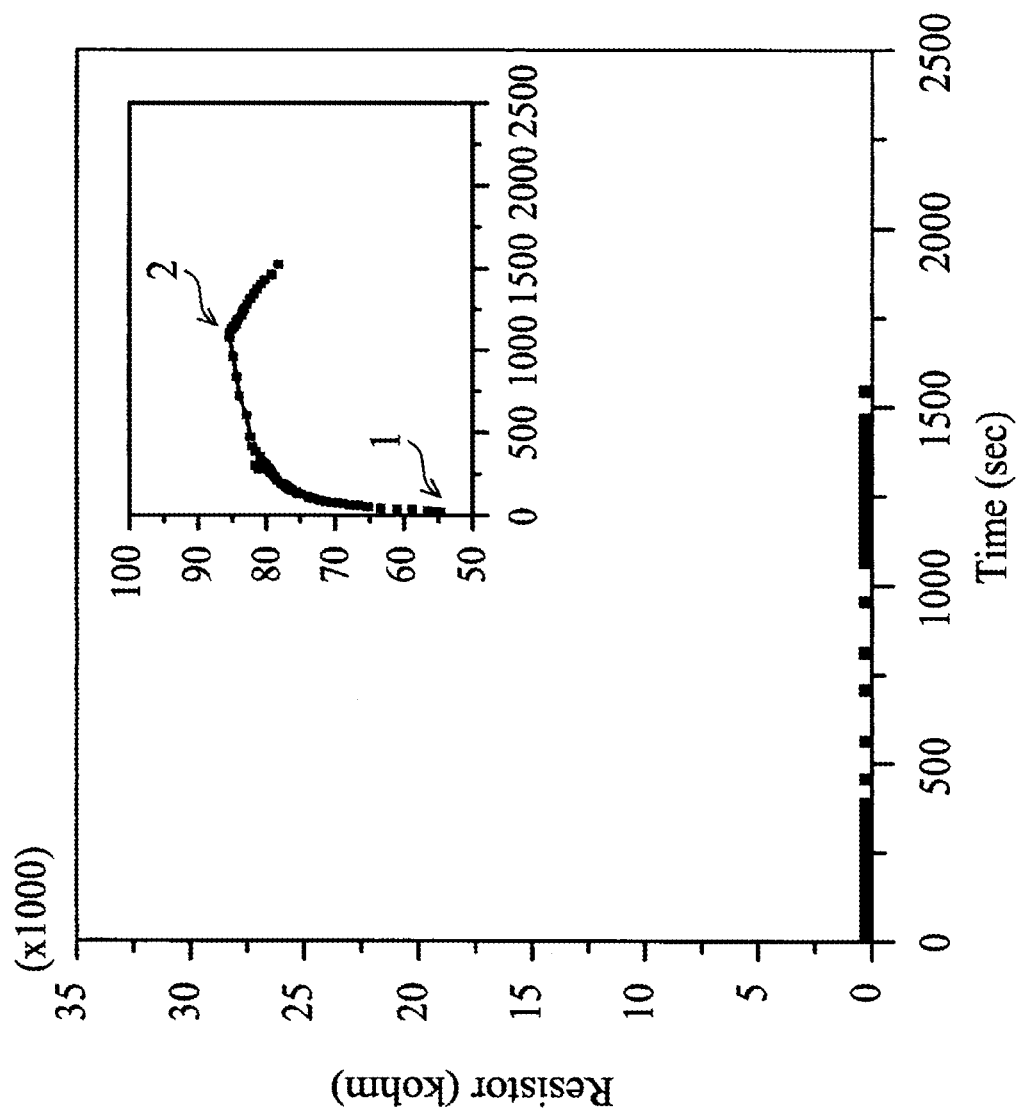
FIG. 4 illustrates the characteristic curve of a conventional $SnO_2$ gas sensor to 1010 ppm $NO_2$ gas.

FIGS. 3 and 4 respectively compare the characteristic curves of the gas sensor of the present invention and the conventional $SnO_2$ gas sensor to 1010 ppm $NO_2$ gas. The coordinates in FIGS. 3 and 4 are the same, with mark 1 indicating initialized the input of $NO_2$ and mark 2 stoppage. The right upper plate of FIG. 4 illustrates the amplified signal.

The gas sensors prepared in Examples 1 and 2 were evaluated at room temperature for characteristics such as sensitivity, recovery time, and repeatability, wherein sensitivity indicates the ratio of finally achieved, stable resistor value ($R_{gas}$) to the original resistance value ($R_{air}$) with the exposure of 1010 ppm $NO_2$, recovery time indicates the time for the gas sensor to recover the resistance value to the original value after stopping input of 1010 ppm $NO_2$, and repeatability indicates curve changes for two subsequent detections of 1010 ppm $NO_2$.

According to the above defined characteristics, it is clear that the conventional gas sensor has no sensitivity at room temperature, as shown in FIG. 4. The results from the gas sensor of the present invention shown in FIG. 3 indicate that sensitivity of 480 at room temperature with recovery time about 2 minutes. Moreover, the subsequent two detection curves shown in FIG. 3 are similar, indicating that the gas sensor of the present invention has good repeatability.

With a simple combination of tin oxide with a small amount of carbon nanotubes, the gas sensor of the present invention provides high sensitivity, short recovery time and excellent repeatability. In addition, the cost of the gas sensor of the present invention is low since additional heating devices for desorption of gas on the sensing film is not required.

While the invention has been particularly shown and described with the reference to the preferred embodiments thereof, it will be understood by those skilled in the art that various changes in form and details may be made without departing from the spirit and scope of the invention.

What is claimed is:

1. A manufacturing method of a gas sensor, comprising:
   (a) providing a substrate with a pair of electrodes thereon;
   (b) coating a mixture of carbon nanotubes and a tin-containing organo-metallic solution on the substrate to fully cover the electrode;
   wherein the tin-containing organo-metallic solution is formed by solubilizing tin (II)-2-ethylhexanoate in 2-ethylhexanoic acid; and
   wherein the tin (II)-2-ethylhexanoate in the tin-containing organo-metallic solution is 5% to 20% by weight, and the carbon nanotubes in the organo-metallic solution are 0.0005% to 0.1% by weight; and (c) oxidizing the mixture to obtain a gas sensing porous thin film composed of carbon nanotubes and tin oxide, wherein the oxidizing step is performed at 400 to 700° C. for 20 to 60 minutes.

2. The manufacturing method as claimed in claim 1, wherein the substrate is insulating material or semiconductor material.

3. The manufacturing method as claimed in claim 2, wherein the substrate is ceramic material.

4. The manufacturing method as claimed in claim 3, wherein the ceramic material is glass, aluminum oxide, silicon oxide, quartz, or mica.

5. The manufacturing method as claimed in claim 2, wherein the semiconductor material is silicon.

6. The manufacturing method as claimed in claim 1, wherein the electrode is gold, platinum, or silver.

7. The manufacturing method as claimed in claim 1, wherein the carbon nanotubes are single-walled carbon nanotubes (SWCNTs).

8. The manufacturing method as claimed in claim 1, wherein the carbon nanotubes are multi-walled carbon nanotubes (MWCNTs).

9. The manufacturing method as claimed in claim 1, wherein the carbon nanotubes are dispersed in the tin-containing organo-metallic solution by ultrasonic or mechanical vibration.

10. The manufacturing method as claimed in claim 1, wherein the mixture application is performed by spin coating, dip coating, screen printing, or spraying.

11. The manufacturing method as claimed in claim 1, wherein the electrode has a comb, strip, or helix shape.

12. The manufacturing method as claimed in claim 1, further comprising coating an Ag/Pd layer on the end of each electrode.

13. The manufacturing method as claimed in claim 12, further comprising connection of the Ag/Pd layer separately to a signal line.

\* \* \* \* \*